(12) United States Patent
den Hoed

(10) Patent No.: US 11,060,122 B2
(45) Date of Patent: Jul. 13, 2021

(54) METHOD OF PRODUCING JELLYFISH COLLAGEN EXTRACT

(71) Applicant: Robert den Hoed, Sioux Center, IA (US)

(72) Inventor: Robert den Hoed, Sioux Center, IA (US)

( * ) Notice: Subject to any disclaimer, the term of this patent is extended or adjusted under 35 U.S.C. 154(b) by 449 days.

(21) Appl. No.: 15/591,301

(22) Filed: May 10, 2017

(65) Prior Publication Data

US 2018/0327799 A1 Nov. 15, 2018

(51) Int. Cl.
| | |
|---|---|
| *C12P 21/00* | (2006.01) |
| *C07K 14/78* | (2006.01) |
| *C12P 13/24* | (2006.01) |
| *C12P 19/26* | (2006.01) |
| *C12P 19/02* | (2006.01) |
| *C12P 19/04* | (2006.01) |

(52) U.S. Cl.
CPC .............. *C12P 21/00* (2013.01); *C07K 14/78* (2013.01); *C12P 13/24* (2013.01); *C12P 19/02* (2013.01); *C12P 19/04* (2013.01); *C12P 19/26* (2013.01); *C12Y 304/00* (2013.01)

(58) Field of Classification Search
CPC ........ C12P 21/00; C07K 14/78; C12Y 304/00
See application file for complete search history.

(56) References Cited

U.S. PATENT DOCUMENTS

| | | | | |
|---|---|---|---|---|
| 3,875,138 A | * | 4/1975 | Jackson | C07K 14/605 |
| | | | | 530/304 |
| 4,389,487 A | * | 6/1983 | Ries | A61K 8/65 |
| | | | | 128/DIG. 8 |
| 5,411,887 A | * | 5/1995 | Sjolander | C07K 14/78 |
| | | | | 435/273 |
| 2005/0271614 A1 | * | 12/2005 | Wolfinbarger, Jr. | A23J 1/04 |
| | | | | 424/70.14 |
| 2009/0069217 A1 | * | 3/2009 | Kato | A61K 31/375 |
| | | | | 514/1.1 |
| 2011/0068106 A1 | * | 3/2011 | Zukor | B01L 3/50825 |
| | | | | 220/367.1 |
| 2011/0077382 A1 | * | 3/2011 | Tang | A61K 8/65 |
| | | | | 530/356 |
| 2015/0094219 A1 | * | 4/2015 | Trowell | C12Q 1/66 |
| | | | | 506/9 |
| 2016/0010890 A1 | * | 1/2016 | Suzuki | F24H 4/04 |
| | | | | 62/160 |
| 2016/0120955 A1 | * | 5/2016 | Gueta | A61K 38/39 |
| | | | | 424/530 |

FOREIGN PATENT DOCUMENTS

| | | | | |
|---|---|---|---|---|
| CN | 1721546 A | * | 1/2006 | |
| JP | 2001178492 A | * | 7/2001 | |
| JP | 2007051191 A | * | 3/2007 | |

OTHER PUBLICATIONS

Machine translation of CN-1721546-A (2006) downloaded from ProQuest on Mar. 2, 2018. (Year: 2006).*
Negai et al. J. Sci. Food Agric. (1999) 79: 855-858 (Year: 1999).*
Silva et al. Ind. Eng.Chem. Res. (2016) 55: 6922-6930 (Year: 2016).*
Translation of JP 2007051191, published Mar. 2007 (Year: 2007).*
Translation of JP-2001178492 published Jul. 2001 (Year: 2001).*
"Water & More" webpage (2016) downloaded from http://www.waterand more hub.com/deionized-water-vs-distilled-water downloaded Aug. 21, 2018 (Year: 2016).*

* cited by examiner

*Primary Examiner* — Susan M Hanley
(74) *Attorney, Agent, or Firm* — Zarley Law Firm, P.L.C.

(57) ABSTRACT

A method of producing jellyfish collagen extract by combining hard water, frozen jellyfish, protease enzymes, and sodium bisulfate to form a mixture. Heating the mixture for a period of time to permit the mixture to react. The filter, concentrate, and dry the mixture.

20 Claims, 2 Drawing Sheets

METHOD OF PRODUCING JELLYFISH COLLAGEN EXTRACT

BACKGROUND OF THE INVENTION

This invention is directed to a method of producing a collagen extract, and more particularly making a collagen extract from jellyfish.

Collagen extracts are well known in the art and are used to improve health. Use of jellyfish as a source for collagen has been avoided due to safety concerns. Recent testing, however, has confirmed that the jellyfish collagen would not cause any undue harm if ingested by man and animal, quite the opposite actually. Adding to the safety aspect, this collagen source is of value if one is concerned about the overall safety of bovine collagen due to problems associated with the possible transmission of bovine spongiform encephalopathy (BSE) and transmissible spongiform encephalopathy (TSE).

Due to the evolutionary ancient lineage of jellyfish collagen specific to actual direct specific typing it is based on comparative collagen aspects by instrumentation. The collagen behaves as vertebrate "Type II" and "Type I" which is based on initial analysis (SDS. FITR). The collagen also is fibrillar in nature, possesses $\alpha 1$ and $\alpha 2$ chains and has identical FITR spectra to other collagen (rat tail, bovine). The ASC and PSC extracted in its entirety would be similar to that of type 1 collagen (mammalian). Furthermore the jellyfish collagen examined also showed of "comparable" attributes to vertebrate collagen IV or V and exhibited a very unique structure with a fourth "a-chain". The specifics of this testing was further enhanced by a matching of the electrophoretic patterns, fully backing up the FTIR analysis.

The technical aspects of this non bovine/avian collagen carries a distinctive broad collagen typing that has a wide range of positive effects on health and aging. Given the bio-availability of this jellyfish collagen and its biological properties, this material is also an excellent candidate for the replacement of bovine or other collagen sources targeted biomedical applications on its merit alone.

The MBI Jellyfish collagen in our opinion appears to be a very unique formed collagen substance. The attributes of which could prove to present a wide array of uses clinically which is currently being evaluated.

In particular, jellyfish collagen extract is believed to have a beneficial effect on brain and cellular health such as reducing Alzheimer's and dementia. In particular, the extract permits improved nutrient and calcium binding as well as excretion of metabolic waste. Also, type I, II, IV and V collagen improves motor skills. Therefore, a need exists for a method of producing jellyfish collagen extract.

Therefore, an objective of the present invention is to provide a method of producing a jellyfish collagen extract.

Another objective of the present invention is to provide a method of producing a collagen extract that reduces dementia.

These and other objectives will be apparent to one of ordinary skill in the art based upon the following written description, drawings, and claims.

SUMMARY OF THE INVENTION

A method of producing jellyfish collagen extract where frozen jellyfish, hard water, protein enzymes, and sodium bisulfate are combined in a tank to form a mixture. The mixture is then heated for a period of time to permit the contents of the mixture to react.

Next the mixture is filtered to remove sediment and leave a cloudy liquid. The cloudy liquid is then concentrated through ultrafiltration and/or evaporation to form a solid. The solid is dried to form the collagen extract.

DETAILED DESCRIPTION OF THE PREFERRED EMBODIMENT

Figure 1:
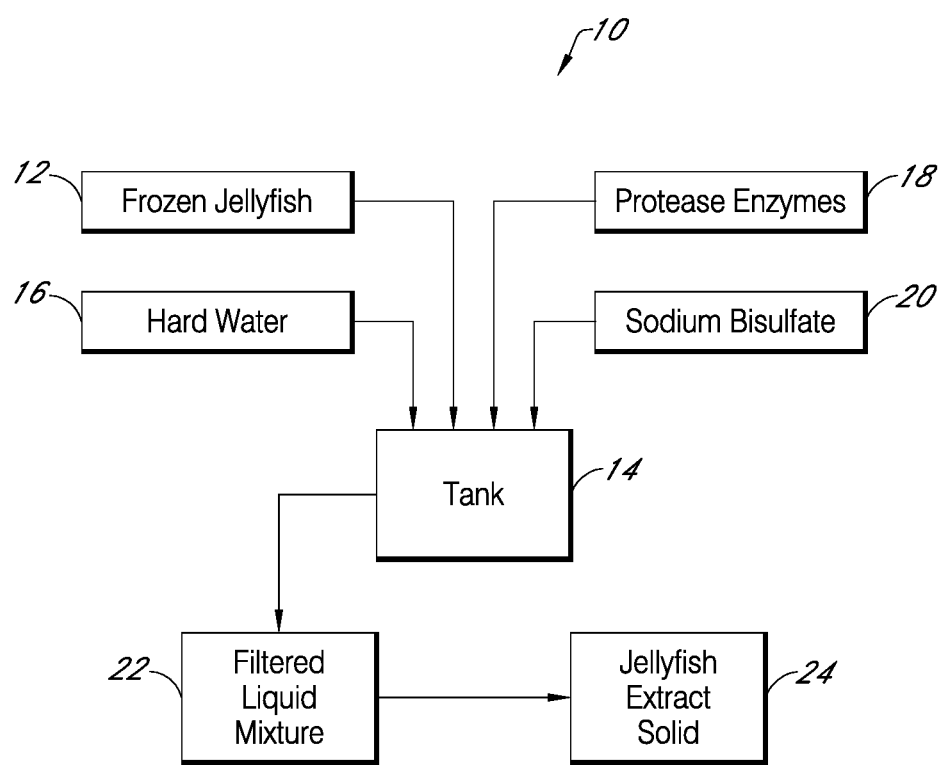
FIG. 1 is a schematic view of the environment of a method for producing a jellyfish collagen extract.
Figure 2:
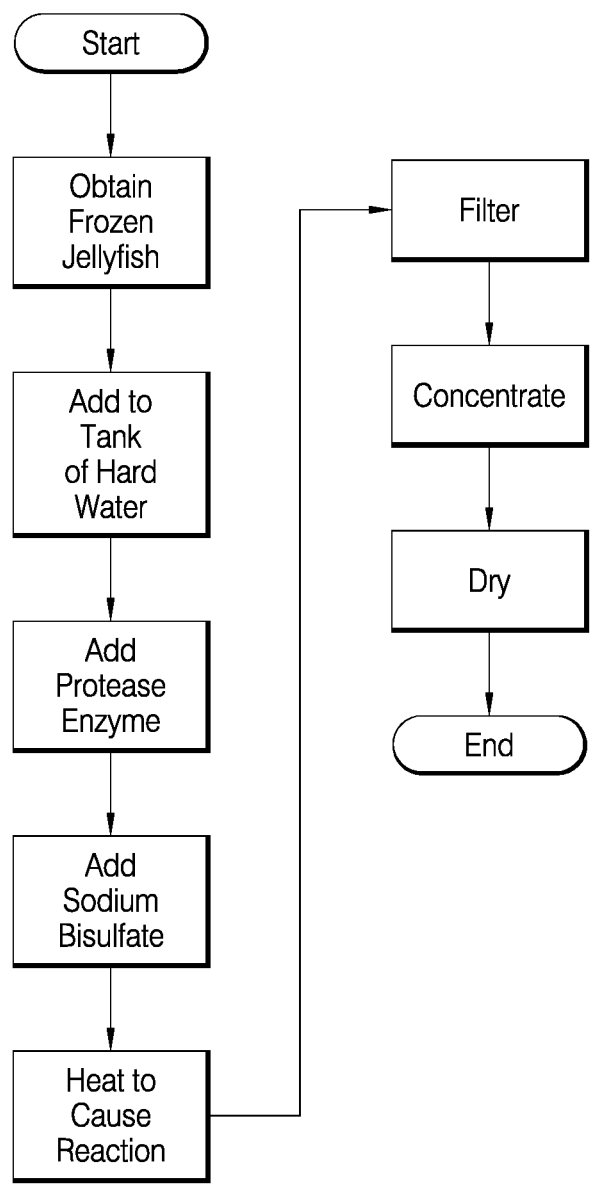
FIG. 2 is a flow diagram for a method of producing a jellyfish collagen extract.

Referring to the Figures, a method of making collagen from jellyfish 10 begins by obtaining a quantity of frozen jellyfish 12. In a preferred example, 1,026,000 grams of cannonball frozen jellyfish 12 are obtained. The frozen jellyfish 12 is added to a heated tank 14 holding a quantity of hard water 16 where calcium has been removed from the water. Preferably 410 grams of hard water 16 is in the tank.

A mixture of protease enzymes 18 and sodium bisulfate 20 are then added to the tank 14. The protease enzymes 18 are of any type and preferably are between 0.005 to 5 percent of volume to weight of the contents of the tank and ideally 2 percent. In a preferred embodiment the enzymes 18 comprise 10,480 mls of 660 L protease enzyme and 3,496 mls of 14 L protease enzyme. The sodium bisulfate 20 is preferably 0.05 to 3 percent weight to weight of the content of the tank and ideally is 1 percent. Preferably 4,640 mls of sodium bisulfate is added.

The contents of the tank 14 is then heated to 60° C. which is maintained for between 2 and 20 hours to permit the contents of the tank to react with one another.

Upon completion, the contents of the tank is filtered to remove sediment and leave a cloudy liquid mixture 22. The cloudy liquid mixture 22 is then concentrated through ultrafiltration and/or evaporation to produce a jellyfish extract solid 24. Preferably, the period for evaporation is between thirty minutes and twenty hours. The jellyfish extract solid is preferably between five and fifty percent of the concentrate. The jellyfish extract solid 24 is then dried, such as by spray drying.

The resulting jellyfish extract collagen aequorin which is a calcium binding protein, calmodulin which is also a calcium binding protein, coelenterazine which is a calcium binding protein component, various amino acids, Type I, II, IV and V collagen, and mucopolysacchides including chondroitin sulfate and hyaluronic acid.

Testing produced the following protein breakdown.

| Collagen Acid Soluble Protein Breakdown | % - Percentile |
| --- | --- |
| 3-Hydroxyproline | 0.1 |
| 4-Hydroxyproline | 4.5 |
| Aspartic acid | 7.8 |
| Threonine | 3.1 |
| Serine | 4.6 |
| Glutamic acid | 9.7 |
| Proline | 7.5 |
| Glycine | 30.2 |
| Alanine | 7.8 |
| Half-cystine | 0.6 |
| Valine | 3.1 |
| Methionine | 1.3 |
| Isoleucine | 2.1 |
| Leucine | 3.2 |

-continued

| Collagen Acid Soluble Protein Breakdown | % - Percentile |
|---|---|
| Tyrosine | 0.9 |
| Phenylalanine | 1.2 |
| Tryptophan | 0.1 |
| Hydoxylysine | 3.2 |
| Lysine | 3.1 |
| Histidine | 0.7 |
| Arginine | 5.2 |

In addition, testing showed that the method produced 2103 pmol/µg of Coelenterazine, 2011 mg/kg of Aequorin (DM) and 406 mg/kg of Calmodulin (Extractable). Finally, through testing, the method produced the following analyte in the jellyfish collagen extract.

| Analyte | Result | Unit |
|---|---|---|
| Chondroitin Sulfate | 10.59 | % wt |
| Glucosamine | 0.19 | % wt |
| Hyaluronic Acid | 3.21 | % wt |
| Hydroxyproline | 6.58 | % wt |
| Mucopolysaccharides | 29-40 | % wt |

Accordingly, a method of making jellyfish collagen extract has been disclosed that, at the very least, meets all the stated objectives.

What is claimed is:

1. A method of producing jellyfish collagen extract, comprising the steps of:
    obtaining a quantity of frozen jellyfish;
    adding the frozen jellyfish to a tank containing hard water;
    adding protease enzymes and sodium bisulfate to the tank to form a mixture;
    heating the tank to 60° C. for a period of time that permits a reaction in the mixture;
    filtering the mixture to remove sediment concentrate from the mixture to form a solid; and
    drying the solid to form a jellyfish collagen extract.

2. The method of claim 1 wherein a period between two and twenty hours permits the mixture to react.

3. The method of claim 1 wherein the mixture is concentrated through ultrafiltration.

4. The method of claim 1 wherein the mixture is concentrated through evaporation.

5. The method of claim 1 wherein the solid is spray dried.

6. The method of claim 1 wherein the jellyfish collagen extract includes type I, II, IV, and V collagen.

7. The method of claim 1 wherein the jellyfish collagen extract includes Aequorin, Calmodulin, and Coelenterazine.

8. The method of claim 1 wherein the jellyfish collagen extract includes mucopolysaccharides.

9. The method of claim 8 wherein the mucopolysaccharides include chondroitin and hyaluronic acid.

10. The method of claim 1 wherein the jellyfish collagen extract includes calcium binding proteins.

11. The method of claim 1 wherein the jellyfish collagen extract having 10.59% wt of chondroitin sulfate, 0.19% wt of glucosamine; 3.21% wt of hyaluronic acid, 6.58% wt hydroxyproline, and 29 to 40% wt of mucopolysaccharides.

12. The method of claim 1 wherein the jellyfish collagen extract having 2103 pmol/µg of coelenterazine, 2011 mg/kg of aequorin, and 406 mg/kg of calmodulin.

13. The method of claim 1 wherein the jellyfish collagen extract having a collagen acid soluble protein breakdown of 0.1% 3-hydroxyproline, 4.5% 4-hydroxyproline, 7.8% aspartic acid, 3.1% threonine, 4.6% serine, 9.7% glutamic acid, 7.5% proline, 30.2% glycine, 7.8% alanine, 0.6% half-cystine, 3.1% valine, 1.3% methionine, 2.1% isoleucine, 3.2% leucine, 0.9% tyrosine, 1.2% phenylalanine, 0.1% tryptophan, 3.2% hydoxylysine, and 3.1% lysine.

14. A method of producing jellyfish collagen extract, comprising the steps of:
    obtaining a quantity of frozen jellyfish;
    adding water to a tank, wherein calcium has been removed from the hard water prior to being added to the tank;
    adding the frozen jellyfish to the tank;
    adding protease enzymes and sodium bisulfate to the tank to form a mixture;
    heating the tank to 60° C. for a period of time that permits a reaction in the mixture;
    filtering the mixture to remove sediment concentrate from the mixture to form a solid; and
    drying the solid to form a jellyfish collagen extract.

15. The method of claim 14 wherein the jellyfish collagen extract includes calcium binding proteins.

16. The method of claim 14 wherein the jellyfish collagen extract having 10.59% wt of chondroitin sulfate, 0.19% wt of glucosamine; 3.21% wt of hyaluronic acid, 6.58% wt hydroxyproline, and 29 to 40% wt of mucopolysaccharides.

17. The method of claim 14 wherein the jellyfish collagen extract having 2103 pmol/µg of coelenterazine, 2011 mg/kg of aequorin, and 406 mg/kg of calmodulin.

18. The method of claim 14 wherein the jellyfish collagen extract having a collagen acid soluble protein breakdown of 0.1% 3-hydroxyproline, 4.5% 4-hydroxyproline, 7.8% aspartic acid, 3.1% threonine, 4.6% serine, 9.7% glutamic acid, 7.5% proline, 30.2% glycine, 7.8% alanine, 0.6% half-cystine, 3.1% valine, 1.3% methionine, 2.1% isoleucine, 3.2% leucine, 0.9% t tyrosine, 1.2% phenylalanine, 0.1% tryptophan, 3.2% hydoxylysine, and 3.1% lysine.

19. A method of producing jellyfish collagen extract, comprising the steps of:
    obtaining a quantity of frozen jellyfish;
    adding the frozen jellyfish to a tank containing water;
    adding protease enzymes and sodium bisulfate to the tank to form a mixture;
    heating the tank for a period of time that permits a reaction in the mixture;
    filtering the mixture to remove sediment concentrate from the mixture to form a solid; and
    drying the solid to form a jellyfish collagen extract.

20. The method of claim 1 wherein the sodium bisulfate is between 0.05 and 3 percent weight to weight of the mixture.

* * * * *